United States Patent [19]
Royalty et al.

[11] Patent Number: 5,585,329
[45] Date of Patent: Dec. 17, 1996

[54] PLANT GROWTH PROMOTION USING 3-CYANO-1-PHENYLPYRAZOLES SUCH AS FIPRONIL

[75] Inventors: Reed N. Royalty, Raleigh, N.C.; Nguyen D. Long, Hochiminville, Viet Nam; Michael T. Pilato; Nicholas M. Hamon, both of Cary, N.C.

[73] Assignee: Rhone-Poulenc Inc., Research Triangle Park, N.C.

[21] Appl. No.: 430,499

[22] Filed: Apr. 28, 1995

[51] Int. Cl.$^6$ .................................................. A01N 43/56
[52] U.S. Cl. ............................................................. 504/282
[58] Field of Search ............................................. 504/282

[56]  References Cited

U.S. PATENT DOCUMENTS

| | | | |
|---|---|---|---|
| 4,614,533 | 9/1986 | Schallner et al. | 71/92 |
| 4,787,930 | 11/1988 | Gehring et al. | 71/92 |
| 5,232,940 | 8/1993 | Hatton et al. | 514/407 |

FOREIGN PATENT DOCUMENTS

| | | |
|---|---|---|
| 0295117 | 12/1988 | European Pat. Off. . |
| 2696904 | 4/1994 | France . |
| 87/03781 | 7/1987 | WIPO . |
| 93/06089 | 4/1993 | WIPO . |
| 94/21606 | 9/1994 | WIPO . |

OTHER PUBLICATIONS

Grow World Crop Protection News, No. 244, Nov. 17, 1995, p. 8.
*Arthropod Management Tests,* vol. 20, report No. 99F, p. 225, Entomological Society of America, Special Publication, published no earlier than Jul. 10, 1995 (Bernhardt).
*Arthropod Management Tests,* vol. 20, report No. 100F, pp. 225–226, Entomological Soceity of America, Special Publication, published no earlier than Jul. 10, 1995 (Bernhardt).
*Arthropod Management Tests,* vol. 20, report No. 101F, p. 226, Entomological Soceity of America, Special Publication, published no earlier than Jul. 10, 1995 (Bernhardt).
*Arthropod Management Tests,* vol. 20, report No. 103F, pp. 227–228, Entomological Society of America, Special Publication, published no earlier than Jul. 10, 1995 (Pairang et al).
*Arthropod Management Tests,* vol. 20, report No. 104F, p. 228, Entomological Society of America, Special Publication, published no earlier than Jul. 10, 1995 (Way et al).

*Primary Examiner*—S. Mark Clardy
*Attorney, Agent, or Firm*—Burns, Doane, Swecker & Mathis, L.L.P.

[57]  ABSTRACT

This invention relates to a new method of plant growth promotion whereby a 1-phenylpyrazole such as fipronil is applied to a crop or a seed.

15 Claims, No Drawings

PLANT GROWTH PROMOTION USING 3-CYANO-1-PHENYLPYRAZOLES SUCH AS FIPRONIL

The present invention relates to a new method of treatment of plant which is able to induce growth regulating responses.

The term "method for regulating plant growth" or the term "growth regulation process" or the use of the words "growth regulation" or other terms using the word "regulate" as used in the instant specification mean a variety of plant responses which attempt to improve some characteristic of the plant as distinguished from pesticidal action, the intention of which is to destroy or stunt a growth of a plant or a living being. For this reason the compounds used in the practice of this invention are used in amounts which are non-phytotoxic with respect to the plant being treated.

Plant growth regulation is a desirable way to improve plants and cropping so as to obtain better plants and better conditions of agriculture practices.

More precisely, the present invention relates to the use of certain pyrazole compounds in order to induce growth regulating responses.

The present invention involves the inducement of, as well as the method to induce a plant regulating response through the application of compounds to the plant or the seed or at the plant site having the following generic formula:

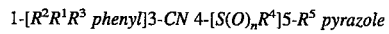

$$1\text{-}[R^2R^1R^3 \text{ phenyl}]3\text{-}CN\ 4\text{-}[S(O)_nR^4]5\text{-}R^5 \text{ pyrazole} \quad (I)$$

wherein $R^1$ and $R^2$ may represent a hydrogen or halogen atom in the 2 and/or 6 position on the phenyl ring (at least one of them is preferably other than hydrogen), $R^3$ may represent a halogen atom or a haloalkyl or haloalkoxy or $SF_5$ group, in the 4 position on the phenyl ring, $R^4$ may represent an alkyl or haloalkyl group, $R^5$ may represent an amino group which may be mono- or di- substituted by an alkyl or haloalkyl radical, acyl, alkoxycarbonyl, n is 0, 1 or 2.

The alkyl, alkoxy or acyl groups of the formula (I) are preferably lower alkyl, alkoxy or acyl, that is to say radicals having one to four carbon atoms.

A preferred group of plant growth regulating effective 1-arylpyrazoles of the present invention are those wherein:

$R^1$ and $R^2$ are a halogen atom,
$R^3$ is 4-haloalkyl
$R^4$ is lower haloalkyl and $R^5$ is amino.

Specific pyrazole derivatives usable in the method for regulating plant growth falling within the scope of the present invention include 1-[2,6-$Cl_2$ 4-$CF_3$ phenyl]3-CN 4-[SO-$CF_3$]5-$NH_2$ pyrazole (preferred plant growth regulator hereafter called compound A).

The preparation of compounds of formula (I) may be made according to any process described in patent applications WO 87/3781, 93/6089, 94/21606 as well as in European patent application 295117, or other process according to the knowledge of a man skilled in the art of chemical synthesis.

The 1-arylpyrazoles used in the process of the present invention have been found to display a wide variety of plant growth regulating properties, depending upon the concentration used, the formulation employed and the type of plant species treated.

By virtue of the practice of the present invention a wide variety of plant growth responses, including the following a. more developed root system
b. tillering increase
c. increase in plant height
d. bigger leaf blade
e. less dead basal leaves
f. stronger tillers
g. greener leaf color
h. less fertilizers needed
i. less seeds needed
j. more productive tillers
k. less third non productive tillers
l. earlier flowering
m. early grain maturity
n. less plant verse (lodging)
o. increased shoot growth
p. improved plant vigour
q. early germination.

It is intended that as used in the instant specification the term "method for regulating plant growth" means the achievement of any of the aforementioned sixteen categories of response as well as any other modification of plant, seed, fruit, vegetable (whether the fruit or vegetable is unharvested or have been harvested) so long as the net result is to increase growth or benefit any property of the plant, seed, fruit or vegetable as distinguished from any pesticidal action (unless the present invention is practiced in conjunction with or in the presence of a herbicide). The term "fruit" as used in the instant specification is to be understood as meaning anything of economic value that is produced by the plant.

Certain preliminary details connected with the foregoing sixteen categories should make for a better appreciation of the invention.

Description of possible formulations may be found in patent applications WO 3781, 93/6089, 94/21606 as well as in European patent application 295117. The formulations described in said prior art are mainly designed for insecticidal purposes. Formulations or compositions for plant growth regulating uses may be made in a similar way, while adapting the ingredients to make them more suitable to the plant or soil to which the application is made.

As examples of crops which might be modified by plant growth regulating action, there are vegetables, rice, corn, cereals or turf.

The 1-arylpyrazoles of this invention may be effective for plant growth regulating purpose when applied to the foliage of plants and/or to the soil in which said plants are growing. These applications are often in the form of granules and are usually applied in sufficient amount to provide a rate of from about 0.005 kg/ha to about 0.5 kg/ha of active ingredient, preferably between 0.01 and 0.2 kg/ha.

The 1-arylpyrazoles of this invention may also be effective for plant growth regulating purpose when applied to the seeds before sowing. The seed may be treated, especially by coating or embedding or impregnation or soaking or dipping in liquid or paste formulations which are known per se and are subsequently dried. Seed comprising 2 to 1000 gram per quintal of seed, preferably 5 to 800 g/q are particularly appropriate.

Advantageously, the above-said 1-arylpyrazoles may also be formulated as flowable compositions, wettable powders, microemulsions and the like, all of which lend themselves to soil, water and/or foliage application and provide the requisite plant growth regulating action. Such formulations include the compounds of the invention admixed with inert, agriculturally-acceptable solid or liquid diluents.

Further description of possible formulations may be found in patent applications WO 87/3781, 93/6089, 94/21606 as well as in European patent application 295117. The formulations described in said prior art are mainly designed for insecticidal purposes. Formulations or compositions for plant growth regulating uses may be made in a similar way, while adapting the ingredients to make them more suitable for use with plant growth regulating action.

For example, wettable powders and granules concentrate formulations of the invention can be prepared by grinding together an 1-arylpyrazole compound of formula (I), with about 1% to 20% by weight of a solid anionic surfactant. One suitable anionic surfactant is a dioctyl ester of sodium sulfosuccinic acid. About 85% to 95%, by weight, of an inert solid diluent, such as montmorillonite, attapulgite, chalk, talc, kaolin, diatomaceous earth, limestone, silicates or the like is also included in such formulations, as well as other adjuvants as previously indicated.

In addition to the granules and wettable powder formulations described hereinabove, flowable formulations may be used since they are readily dispersible in water and may be applied to the proper locus where the plant growth regulating action is expected.

For example, wettable powders and granules concentrate formulations of the invention can be prepared by grinding together an 1-arylpyrazole compound of formula (I), with about 1% to 30% by weight of a solid anionic surfactant. One suitable anionic surfactant is a dioctyl ester of sodium sulfosuccinic acid. About 65% to 98%, by weight, of an inert solid diluent, such as montmorillonite, attapulgite, chalk, talc, kaolin, diatomaceous earth, limestone, silicates or the like is also included in such formulations, as well as other adjuvants as previously indicated.

In addition to the granulated concentrates and wettable powder formulations described hereinabove, flowable formulations may be used since they are readily dispersible in water and may be applied to the breeding grounds, food supply or habitat of the mollusks sought to be controlled. Thus the above-said 1-arylpyrazoles may be advantageously formulated as flowable compositions, suspensions, microsuspensions, suspoemulsions, wettable powders, microemulsions and the like, all of which lend themselves to soil, water and/or foliage application and provide the requisite plant protection. Such formulations include the compounds of the invention admixed with inert, agriculturally-acceptable solid or liquid diluents.

The pyrazole derivatives used in the method of the present invention have a low solubility in water but may be used at low doses. So, they can be applied to plants in aqueous solutions or emulsions or, preferably, suspensions composed wholly or partially of water as well as of proper adjuvant. Partial aqueous medium include those formed of water and, for instance, acetone or methyl ethyl ketone. Any liquid medium may be used provided that it is not toxic to the plant, and preferably not to the environment. Where any particular derivative is less water-soluble, it may be solubilized by the use of co-solvents or wetting agents or it may suspended by mean of dispersing agents which may be used simultaneously with surfactants, extenders, etc. Other media, including solids, like talc; will occur to those skilled in the art. The compounds used in the process of this invention may be absorbed onto solid carriers such as vermiculite, attaclay, talc and the like for application via a granular vehicle. Application of diluted water formulations or solids is accomplished using conventional equipment that is well known in the art.

As will be demonstrated in connection with certain examples in this specification, compounds used in the process of the present invention have been quite effective in regulating plant growth and development in connection with a wide variety of plant species at various concentrations of active pyrazole compounds.

The precise amount of pyrazole compound will depend upon the particular plant species being treated. This may be determined by the man skilled in the art with a few experiments and may vary in plant responses depending upon the total amount of compound used, as well as the particular plant species which is being treated. Of course, the amount of pyrazole compound should be non-phytotoxic with respect of the plant being treated.

Although the preferred method of application of the compounds used in the process of this invention is directly to the foliage and stems of plants, it as been deemed that such compounds may be applied to the soil in which the plants are growing, and that such compounds will be root-absorbed to a sufficient extent so as to result in plant responses in accordance with the teachings of this invention.

The compounds used in the process of the present invention are preferably applied to growing plants as set forth in many of the examples in this specification. However, tinder certain circumstances, the compounds used in the process of the present invention are active in seed treatment, for instance, lettuce seeds and oat seeds.

The following examples are illustrative of methods of plant growth regulation according to the invention, but should not be understood as limiting the said instant invention.

EXAMPLE 1

Rice seed was treated by mixing the seed with a suspension concentrate containing 5% w/w of compound A. This mixing resulted in a coated seed which was immediately sown on a 1000 $m^2$ so as to have 30 g/ha of active ingredient. The results are observed from the seedling emergence through to harvest. Some insects were present and killed. Results were observed 35 days after sowing. A 5.4% yield increase was observed with following plant growth regulating effect:greener plants, higher plants, less dead basal leaves, bigger leaf blade, flowering 2 days earlier.

EXAMPLE 2

Example 1 was repeated. Results were observed 60 days after sowing. A 7% yield increase was observed with following plant growth regulating effect:greener plants, higher plants, less dead basal leaves, bigger leaf blade, flowering 2 days earlier, longer panicles, brighter color of grain.

EXAMPLE 3

Example 1 was repeated except that 40 g/ha of active ingredient were applied. Same results were obtained but also stronger tillers were observed as well as less plant verse.

EXAMPLE 4

Example 1 was repeated except that 50 g/ha of active ingredient were applied. Same results were obtained but also a 15% growth tillers increase was observed as well as a 9.5% yield increase.

EXAMPLE 5

Rice seed was sown and the seed bed (acid sulphate soil) was treated (soil treatment) by spraying it with a suspension concentrate containing 5% w/w of compound A. After treatment, transplantation of rice was made as usual. The treatment of seed bed was made 24 days before transplantation. The following plant growth regulating effects were observed:stronger seedlings, flowering 6 days earlier, 25% in tillers increase, harvest 6 days earlier, 100% yield increase.

EXAMPLE 6

Rice seed was sown and the flooded seed bed was treated (soil treatment) by sprinkling granules containing 0.3% w/w of compound A on it. After treatment, transplantation of rice was made as usual. The treatment of seed bed was made 11 days before transplantation. The following plant growth regulating effects were observed: stronger seedlings, 50% in tillers increase, fertilizers reduced by 40 kg urea and 50 kg/ha of superphosphate, 7% yield increase.

EXAMPLE 7

Corn seeds were sown in 3.5 liters pots (six plants per pot). Immediately after sowing, granules containing compound A were spread on the soil. The granules contained 1.5% w/w of active ingredient and they were spread so as to have a dose of 120 g/ha of active ingredient on the soil. Plants were properly watered. One month and one week after, the dry root weight was measured. The root weight is about 42 g for the treated pots and 30 g for the untreated pots.

EXAMPLE 8

Rice seed was germinated 48 hours in water at 30° C. and then sown in pots. After the emergence of the seedlings, granules containing 0.3% w/w of compound A were applied to the soil at rates of 200 and 100 g/ha. No phytotoxicity was observed with any of the formulations or rates. Periodically, sets of pots were harvested and dry weights of the roots were determined. Pyrazole treatments increased the dry root mass per pot by an average of 36% over that of the untreated seedlings 28 days after treatment.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for treating plants in need of growth promotion, comprising applying to said plants, to the seeds from which they grow or to the locus in which they grow, a non-phytotoxic, effective plant growth promoting amount of a compound having the formula:

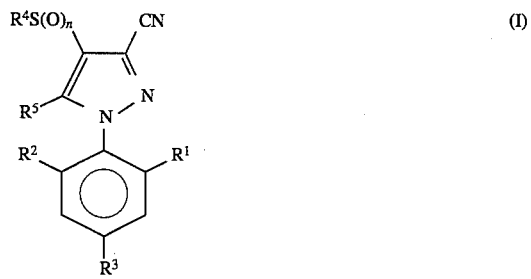

wherein:
  $R^1$ is hydrogen or halogen;
  $R^2$ is hydrogen or halogen;
  $R^3$ is halogen, haloalkyl, haloalkoxy or $SF_5$;
  $R^4$ is alkyl or haloalkyl;
  $R^5$ is amino, which is unsubstituted or which bears one or two substituents selected from the group consisting of alkyl, haloalkyl, acyl and alkoxycarbonyl; and
  n is 0, 1 or 2.

2. A method according to claim 1, wherein at least one of $R^1$ and $R^2$ is halogen.

3. A method according to claim 1, wherein the alkyl, alkoxy, acyl, haloalkyl and haloalkoxy groups have one to four carbon atoms.

4. A method according to claim 1, wherein each of $R^1$ and $R^2$ is halogen, $R^3$ is haloalkyl, $R^4$ is lower haloalkyl and $R^5$ is —$NH_2$.

5. A method according to claim 1, wherein the compound of formula (I) is 5-amino-3-cyano-1-(2,6-dichloro-4-trifluoromethylphenyl)-4-trifluoromethylsulfinylpyrazole.

6. A method according to claim 1, wherein the plant growth promoting amount of the compound of formula (I) applied is sufficient to provide at least one plant growth promoting effect selected from the group consisting of: (a) a more developed root system; (b) a tillering increase; (c) an increase in plant height; (d) a larger leaf blade; (e) fewer dead basal leaves; (f) stronger tillers; (g) a greener leaf color; (h) a need for less fertilizer; (i) a need for fewer seeds; (j) more productive tillers; (k) fewer third nonproductive tillers; (l) earlier flowering; (m) earlier grain maturity; (n) less plant verse; (o) increased shoot growth; (p) improved plant vigor; or (q) earlier germination.

7. A method according to claim 1, wherein the compound of formula (I) is applied to said plants or to the locus in which they grow in the form of granules at an application rate of from about 0.005 kg/ha to about 0.5 kg/ha of compound of formula (I).

8. A method according to claim 7, wherein the application rate is from about 0.01 kg/ha to about 0.2 kg/ha of compound of formula (I).

9. A method for treating plants in need of growth promotion, said plants being selected from the group consisting of rice, corn, cereal and vegetable plants and turf, said method comprising applying to said plants, to the seeds from which they grow or to the locus in which they grow, a non-phytotoxic, effective plant growth promoting amount of a compound having the formula:

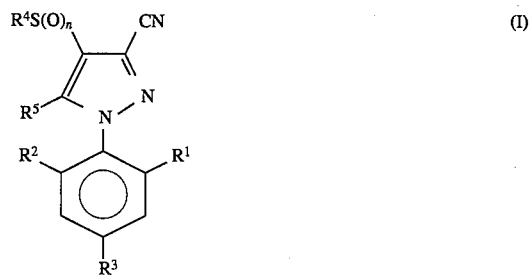

wherein:
  $R^1$ is hydrogen or halogen;
  $R^2$ is hydrogen or halogen;
  $R^3$ is halogen, haloalkyl, haloalkoxy or $SF_5$;
  $R^4$ is alkyl or haloalkyl;
  $R^5$ is amino, which is unsubstituted or which bears one or two substituents selected from the group consisting of alkyl, haloalkyl, acyl and alkoxycarbonyl; and
  n is 0, 1 or 2.

10. A method according to claim 9, wherein the compound of formula (I) is 5-amino-3-cyano-1-(2,6-dichloro-4-trifluoromethylphenyl)-4-trifluoromethylsulfinylpyrazole.

11. A method for treating plants in need of growth promotion, comprising applying to the seeds from which said plants grow, prior to sowing said seeds, a nonphytotoxic, effective plant growth promoting amount of a compound having the formula:

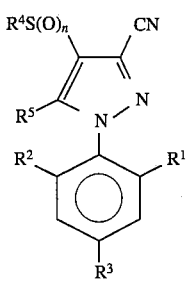

(I)

wherein:

R¹ is hydrogen or halogen;

R² is hydrogen or halogen;

R³ is halogen, haloalkyl, haloalkoxy or $SF_5$;

R⁴ is alkyl or haloalkyl;

R⁵ is amino, which is unsubstituted or which bears one or two substituents selected from the group consisting of alkyl, haloalkyl, acyl and alkoxycarbonyl; and n is 0, 1 or 2.

12. A method according to claim 11, wherein the compound of formula (I) is applied to said seeds at a dose rate of from about 2 to about 1000 grams per quintal of seed.

13. A method according to claim 12, wherein the application rate of the compound of formula (I) is from about 5 to about 800 grams per quintal of seed.

14. A method according to claim 11, wherein the compound of formula (I) is 5-amino-3-cyano-1-(2,6-dichloro-4-trifluoromethylphenyl)-4-trifluoromethylsulfinylpyrazole.

15. A method according to claim 1, wherein the yield is increased.

* * * * *